United States Patent
Saito et al.

(10) Patent No.: US 6,734,021 B1
(45) Date of Patent: May 11, 2004

(54) METHOD AND APPARATUS FOR MEASURING ORGANIC CARBON CONTENT

(75) Inventors: Makoto Saito, Tokyo (JP); Masao Mizuno, Tokyo (JP); Setsuko Kamada, Tokyo (JP)

(73) Assignee: DKK-TOA Corporation, Tokyo (JP)

( * ) Notice: Subject to any disclaimer, the term of this patent is extended or adjusted under 35 U.S.C. 154(b) by 431 days.

(21) Appl. No.: 09/717,149

(22) Filed: Nov. 21, 2000

(30) Foreign Application Priority Data

Nov. 26, 1999 (JP) .......................................... 11-375977

(51) Int. Cl.$^7$ ........................ G01N 33/00; G01N 27/12
(52) U.S. Cl. ................. 436/146; 422/82.01; 422/82.02
(58) Field of Search ....................... 436/146; 422/82.01, 422/82.02

(56) References Cited

U.S. PATENT DOCUMENTS

| | | |
|---|---|---|
| 4,626,413 A | 12/1986 | Blades et al. |
| 4,666,860 A | 5/1987 | Blades et al. |
| 4,775,634 A * | 10/1988 | Sienkiewicz ................ 436/146 |
| 5,518,608 A | 5/1996 | Chubachi |
| 6,444,474 B1 * | 9/2002 | Thomas et al. ............. 436/146 |

FOREIGN PATENT DOCUMENTS

JP    63-46375    9/1988

* cited by examiner

Primary Examiner—Jill Warden
Assistant Examiner—Monique T. Cole
(74) Attorney, Agent, or Firm—Scully Scott, Murphy & Presser

(57) ABSTRACT

The present invention relates to a method and apparatus for measuring the organic carbon content (TOC) in a test liquid by irradiating the test liquid, such as ultrapure water, with ultraviolet radiation and measuring the conductivity of the test liquid that changes due to the produced organic acids and carbon dioxide. After the test liquid is irradiated for a fixed time interval with ultraviolet light in an oxidization process vessel, the irradiation is stopped. The flow rate of the test liquid is such that a portion of test liquid is present that has received the complete irradiation from the commencement to the extinguishing of the lighting of the ultraviolet light source. By controlling the flow rate as above, the ultraviolet light irradiation time of the portion of the test liquid that has received the complete irradiation from the commencement to the extinguishing of the light source equalizes the time from the commencement to the extinguishing of the light without having to carry out precise flow rate control. Therefore, the organic carbon content in the test liquid can be found from the change of the conductivity in this part of the test liquid.

14 Claims, 10 Drawing Sheets

METHOD AND APPARATUS FOR MEASURING ORGANIC CARBON CONTENT

BACKGROUND OF THE INVENTION

1. Field of the Invention

The present invention relates to a method and apparatus for measuring the organic carbon content of, for example, ultrapure water, and in particular to a method and apparatus for measuring the organic carbon content of a test liquid by irradiating the test liquid, such as ultrapure water, with ultraviolet light, and measuring the conductivity of the test liquid, which changes due to generated organic acids and carbon dioxide.

This application is based on Japanese Patent Application, No. Hei 11-375977, the contents of which are incorporated here by reference.

2. Description of Related Art

In modern high precision industrial manufacturing processes, for example, highly purified "ultrapure water" is frequently used in large amounts. For example, washing semiconductors, production of medicines, injections, and the like, and chemical analysis, pure water that contains substantially no impurities such as particles, various species of ions, microorganisms such as bacteria, or soluble substances such as organic compounds, is indispensable. Systems for producing such pure water normally use a combination of reverse osmosis, distillation, ion exchange, absorption processes, vacuum deaeration, ultraviolet oxidizing, and filtration methods including ultrafiltration. In particular, in the field of semiconductor manufacturing, for example, the gaps between circuits are becoming narrower with the increasing density of LSI integration, and thus in order to prevent circuit shorting, the cleaning water for the semiconductors must be of the highest purity, and not only ions, but to the extent possible, particles, bacteria, and organic materials must be eliminated.

One method of indicating the degree of purity of pure water is the TOC (total organic carbon), which represents the degree of contamination using the amount of carbon in the organic substances in the water. As a method of measuring the TOC value of pure water, the TOC measurement using the ultraviolet (UV) oxidizing method is widely used. In this TOC measurement, a test liquid is introduced into an ultraviolet irradiation part, there the test liquid is irradiated with UV light, and the organic carbon in the test liquid is changed into organic acids and carbon dioxide. Then the TOC value of the test liquid is found based on the change in conductivity of the test liquid obtained thereby.

Several types of TOC measurements for such a UV oxidizing are used. For example, the apparatus disclosed in Japanese Examined Patent Application, Second Publication, No. Sho 63-46375, is known. This apparatus irradiates the ultrapure water test liquid resting in a test cell with UV light, and at the same time measures the change in conductivity during this time interval using a conductivity detecting electrode disposed in the test cell. In addition, upon confirming that the oxidizing reaction due to the UV light has substantially completed by using the change in the rate of conductivity, the organic carbon content is found from the amount of change in conductivity up to this point in time.

In addition, an apparatus is known that provides a measuring flow path that disposes first and second conductivity sensors before and after the UV light irradiating part, causes ultrapure water to flow continuously therethrough at a fixed rate of flow, and measures the organic carbon content based on the difference in the conductivity obtained by the first and second conductivity sensors. This apparatus assumes that if the rate of flow of the ultrapure water flowing through the UV light irradiation part is constant, then the amount of UV light that the ultrapure water receives per unit of volume is constant, which implies a constant degree of progress of the oxidizing reaction. In this case, because measurement is carried out while the oxidizing reaction due to the UV light is not complete and the ultrapure water is continuously flowing, the organic carbon content can be continually measured.

Among the above-described former conventional apparatuses using a method wherein the organic carbon content is found from the amount of change in conductivity up to the substantial completion of the oxidizing reaction due to UV light, the following problems are encountered. First, while the time until the completion of the oxidative reaction depends on the components of the test liquid and the strength of the UV light, about 10 to 20 minutes is necessary. Thus, carrying out monitoring of test liquids in real time is difficult.

In addition, because the test liquid is resting in the test cell until the oxidative reaction is complete, eluate from the materials that form the test cell and the conductivity detecting electrode mix into the test liquid, and the conductivity rises. In contrast, the generated carbon dioxide may leak, causing the conductivity to fall. Therefore, the measured values must be compensated by taking into consideration the changes in conductivity that do not depend on the organic carbon content.

Furthermore, because the state of progress of the oxidative reaction is judged by the change of conductivity, a conductivity detecting electrode must always be disposed in the test cell. Thus, the structure of the test cell tends to become complicated and difficult to manufacture.

In contrast, among the above-described latter conventional apparatuses in which the ultrapure water continuously flows at a constant rate of flow, and the organic carbon content is continuously measured based on the difference in conductivity before and after irradiation by UV light, the following types of problems are encountered. First, as described above, being able to measure without the oxidizing reaction having completed assumes that if the rate of flow of ultrapure water flowing through the UV light irradiation part is constant, then the amount of ultraviolet light received per unit of volume of ultrapure water is constant. If the rate of flow of ultrapure water flowing through the UV irradiation means increases, then the amount of UV irradiation per unit of volume of ultrapure water will decrease, and thus the difference in conductivity will become small. In contrast, if the rate of flow decreases, the amount of UV irradiation per unit of volume of the ultrapure water will increase, and thus the difference in conductivity will become large. This means that in the case that the rate of flow of the ultrapure water flowing through the UV irradiation part changes, a measurement error will occur immediately. In order to avoid this type of error, the flow rate control of the ultrapure water must be carried out with extreme precision. As a result, the liquid conveyance system becomes complicated, and the cost of the system as a whole may become high.

Furthermore, in order to observe the difference in conductivity before and after the UV irradiation, two sensors, i.e., the first and second sensor, and the processing circuits for the signals from these sensors, etc., are necessary.

Therefore, in these terms as well, the apparatus becomes complicated and the cost of the system may become high.

In consideration of the above, the present invention has as an object providing a method and apparatus for measurement of the organic carbon content that allows monitoring of the organic carbon amount substantially in real time, and at the same time, does not necessitate precision flow control.

SUMMARY OF THE INVENTION

In order to resolve the above-described problems, controlling the amount of UV light impinging on a flowing test liquid by adjusting the time that the UV light source is lit was investigated. The results showed that if the liquid sample passes through the oxidizing processing vessel below a predetermined rate of flow, a portion of test liquid is present that has received the complete irradiation by UV light from the commencement to the extinguishing of the lighting of the ultraviolet light source, and in this case, the amount of irradiated UV light impinging on the test liquid depends on the time that the UV light source is lit.

Specifically, in order to resolve the above-described problems, the present invention provides a measuring method for the organic carbon content that causes the test liquid to flow into the oxidizing process vessel and stops the irradiation after the UV light has irradiated this test liquid for a predetermined time, measures the base conductivity prior to commencement of the lighting of the UV light and the maximum conductivity after irradiation has stopped with a conductivity detecting means provided in proximity to the exit of the oxidizing vessel, and finds the organic carbon content of the test liquid from the difference between this base conductivity and maximum conductivity, wherein the rate of flow F of the test liquid that flows into the oxidizing vessel, the volume of the part of the oxidizing vessel irradiated by the UV light upstream from the conductivity detecting means, and the irradiation time T of the UV light have the relationship $F \leq V/T$.

Moreover, in the present specification, "in proximity to the exit of the oxidizing vessel", the location where the conductivity direction means is disposed, is meant to include both the inside of the oxidizing process vessel upstream from the exit of the oxidizing process vessel and the outside of the oxidizing process vessel downstream from the same. In addition, in the case of the inside of the oxidizing process vessel, both the area in the part irradiated by the UV light and the area outside the irradiated part are included.

In addition, in the present specification, the "UV light irradiation time T" is not only the time that the complete and continuous irradiation lasts, but includes the time that the irradiation from the light source (for example, a xenon flash lamp) is lit at a constant frequency. This means that the separate flashes during irradiation time T do not correspond to being lit or extinguished or being turned on and turned off.

According to the present invention, portion of test liquid is present that has received the complete irradiation from the commencement to the extinguishing of the lighting of the UV light source, and this shows the maximum conductivity based on the degree of the progress of the oxidizing reaction that depends on the UV irradiation time, and thus the organic carbon content can be found irrespective of fluctuations in the rate of flow.

After this maximum conductivity is measured, preferably the test liquid in the oxidizing vessel is exchanged by increasing the rate of flow at which the test liquid passes through the oxidizing vessel. Thereby, the test liquid that includes oxidized products that remain in the oxidizing vessel can be expelled in a short period of time, and thus the time until the next measurement can be shortened. In addition, even if bubbles are produced in the oxidizing vessel and the conductivity detecting means, when the rate of flow is increased, they can be caused to flow out and be eliminated.

In addition, in order to promote the UV oxidizing of the organic carbon in the test liquid, preferably a photocatalyst is used. Thereby, even with an identical UV light irradiation time, larger fluctuations in conductivity can be obtained, and thus the detection sensitivity can be improved.

In addition, in the case that the amount of UV light is measured and the amount of the measured light is smaller than a predetermined value, a warning can be output. Thereby, the user can be notified about the deterioration of the light source.

In addition, the present invention provides a measuring apparatus for organic carbon content that is characterized in providing an oxidizing process vessel through which the test liquid passes, a UV light source that irradiates the test liquid in the oxidizing process vessel with UV light, a light control means that turns off the UV light source after being lit for a predetermined time, a conductivity detecting means that is provided in proximity to the exit of the oxidizing process vessel, and a calculating means that calculates the organic carbon content in the test liquid from the difference between a base conductivity before commencement of the lighting of the UV light and a maximum conductivity after turning off the UV light source that is measured by this conductivity detecting means, and at the same time provides a flow rate control means that controls the rate of flow F such that the rate of flow F at which the test liquid passes through the oxidizing process vessel, the volume V of the part of the oxidizing process vessel irradiated by the UV light that is upstream from the conductivity detecting means, and the irradiation time of the UV light have the relationship $F \leq V/T$.

According to the present invention, portion of test liquid is present that has received the complete irradiation from the commencement to the extinguishing of the lighting of the ultraviolet light source, and in the conductivity detecting means, a maximum conductivity based on the degree of progress of the oxidizing reaction that depends on the UV light irradiation time interval can be obtained. Thereby, the amount of the organic carbon can be found irrespective of fluctuations of the rate of flow.

As explained above, a means that exchanges the lest liquid in the oxidizing process vessel by increasing the rate of flow of the test liquid passing through the oxidizing process vessel after the maximum conductivity is measured is desirable. In addition, in order to promote the UV oxidizing of the organic carbon in the test liquid, preferably a photocatalyst is provided in the oxidizing process vessel.

In the case that a photocatalyst is provided in the oxidizing process vessel, the oxidizing process vessel is a two-layer pipe structure in which the test liquid passes through the oxidizing vessel between an inner tube comprising a material that substantially transmits UV light and an outer tube, the inside of the outer tube is covered by a photocatalyst, and the UV light source is disposed on the inner tube side. In this case, the UV light source can be accommodated inside the tube, or the outer tube of the UV light source can also act as the inner tube of the oxidizing process vessel.

In addition, preferably the apparatus of the present invention provides a photometer that measures the amount of UV light from the UV light source. Thereby, in the case that the amount of light measured by the photometer falls below a predetermined value, a warning, for example, can be output that notifies the user that it is time to exchange the UV light source. In addition, compensation of the organic carbon content that takes into account the fluctuating and decreasing amount of UV light can also be considered.

Furthermore, the apparatus of the present invention preferably has a means to confirm the rate of flow F of the test liquid that is passing through the oxidizing process vessel. Thereby, in the case that the rate of flow F, the volume V of the part of the oxidizing process vessel that is irradiated by UV light upstream from the conductivity detecting means, and the irradiation time T of the UV light do not maintain the relationship $F \leq V/T$ for any reason, a warning can be issued, for example.

According to the present invention, measurement of the organic carbon content can be performed in the extremely short interval of once every a few minutes. Thus, monitoring of the organic carbon content can be carried out substantially in real time. Furthermore, because precision control of the rate of flow is not necessary in order to obtain the measured values, an apparatus having a simple structure is possible. Therefore, an apparatus for measuring the organic carbon content that is low cost and easy to use can be provided.

BRIEF DESCRIPTION OF THE DRAWINGS

FIG. 7A is a vertical face drawing and FIG. 7B is a horizontal drawing.

FIG. 8A is a vertical face drawing and FIG. 8B is a horizontal drawing.

PREFERRED EMBODIMENTS

Figure 1:
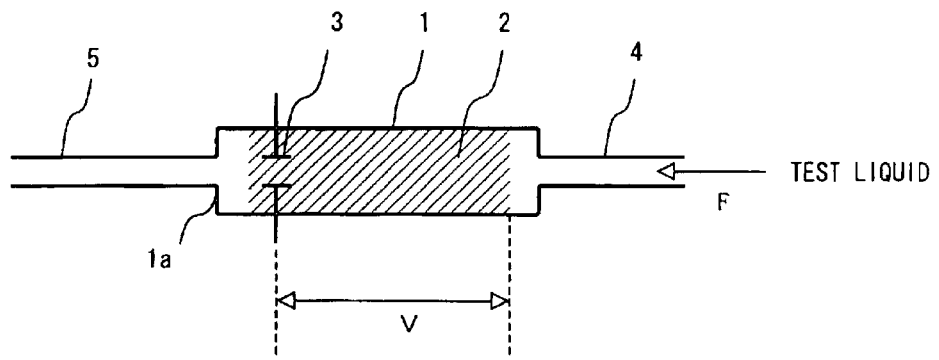
FIG. 1 is a schematic structural drawing of the organic carbon content measuring apparatus according to an embodiment of the present invention.

Below, embodiments of the present invention will be explained referring to the figures. FIG. 1 is a first embodiment of the organic carbon content measuring apparatus according to the present invention. In the oxidizing process vessel 1 through which the test liquid passes, there is a UV light irradiation area 2 (slanted line) that the UV light of a UV light source (not illustrated) irradiates for a predetermined time T. In addition, a conductivity detecting electrode 3 that is the conductivity detecting means in the UV irradiation area 2 is disposed somewhat upstream from by the exit 1a of the oxidizing process vessel 1. The rate of flow F of the test liquid flowing from the entrance pipe 4 to the exit pipe 5 via the oxidizing process vessel 1 can be controlled by a flow rate control means (not illustrated) such that the relationship to the volume V of the UV irradiation area 2 on the side upstream from the conductivity detecting electrode 3 and the irradiation time T of the UV light is $F \leq V/T$.

The configuration of the oxidization process vessel 1 and the UV light source is not particularly limited, but in the examples described in detail below, a configuration wherein the irradiation is performed from within the inner tube of the oxidization process vessel that comprises two tubes is preferably used. In addition, a configuration wherein the UV light source is disposed on the outside surface of the tube-shaped oxidizing process vessel and a configuration wherein a spiral shaped tube serves as the oxidization process vessel on the outside of the tube-shaped UV light source, for example, are among the various configurations that can be suitably used. Moreover, as a UV light source, a mercury lamp can be advantageously used, but the invention is not particularly limited to this, and a xenon flash lamp and a UV lamp with silent discharge, for example, can be used.

Inside the oxidizing process vessel, a photocatalyst for promoting UV oxidizing of the organic carbon is provided. As a photocatalyst, titanium oxide ($TiO_2$) can be most advantageously used, but in addition, $SrTiO_3$, CDS, $WO_3$, $Fe_2O_3$, and $MO_3$, for example, can also be used. To provide the photocatalyst inside the oxidization process vessel, the catalyst can be filled into the vessel as-is, or for example, coated on beads that are filled into the inner wall of the oxidizing process vessel and the inside of the oxidizing process vessel.

In addition, as a flow rate control means, a pump that makes the flow rate constant can be used, but a pressure regulating valve or orifice can be used as a flow rate regulating means for carrying out supply pressure regulation of the test liquid and pressure regulation of back pressure applied to the exit 1a can also be used. In addition, the flow rate control means operates so as to maintain the above-described relationship $F \geq V/T$, and in addition can switch to a flow rate that is larger than this. Specifically, such a function can be attained, for example, by a valve that opens when the flow rate is made high, a switching valve to two flow paths having installed pumps with different rates of flow, or a pump having a variable flow rate.

Figure 2:
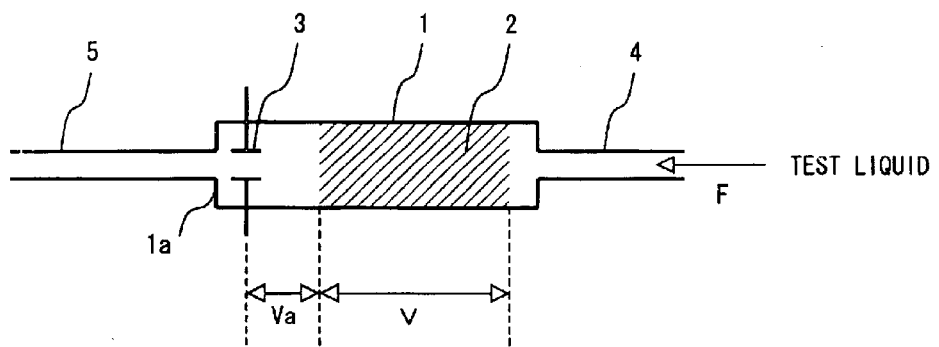
FIG. 2 is a schematic structural drawing of the organic carbon content measuring apparatus according to another embodiment of the present invention.

FIG. 2 is another embodiment of the organic carbon content measuring apparatus according to the present invention. In FIG. 2, essential structural components that are identical to those of FIG. 1 have identical reference numbers and their explanation is omitted. In this embodiment, a conductivity detecting electrode 3 is disposed somewhat upstream from the exit 1a of the oxidizing process vessel 1 and downstream from the UV light irradiation area 2. The rate of flow F can be controlled by the rate flow control means (not illustrated) so as to maintain the relationship $F \geq V/T$ with the volume V of the UV light irradiation area 2 and the irradiation time T of the UV light. Moreover, the volume of test liquid that has passed through the UV light irradiation area 2 and reached the conductivity detecting electrode 3 is denoted Va.

Figure 3:
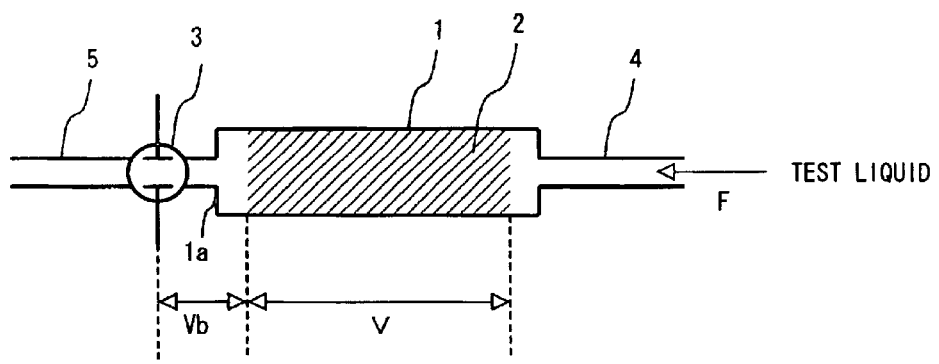
FIG. 3 is a schematic structural drawing of the organic carbon content measuring apparatus according to another embodiment of the present invention.

FIG. 3 is another embodiment of the organic carbon content measuring apparatus according to the present invention. In FIG. 3, essential structural components that are identical to those of FIG. 1 have identical reference numbers and their explanation is omitted. In this embodiment, a conductivity detecting electrode 3 is disposed somewhat downstream from the exit 1a of the oxidization process vessel 1. The rate of flow F can be controlled by the rate flow control means (not illustrated) so as to maintain the relationship $F \geq V/T$ with the volume V of the UV light irradiation area 2 and the irradiation time T of the UV light. Moreover, the volume of test liquid that has passed through the UV light irradiation area 2 and reached the conductivity detecting electrode 3 is denoted Vb.

Figure 4A:
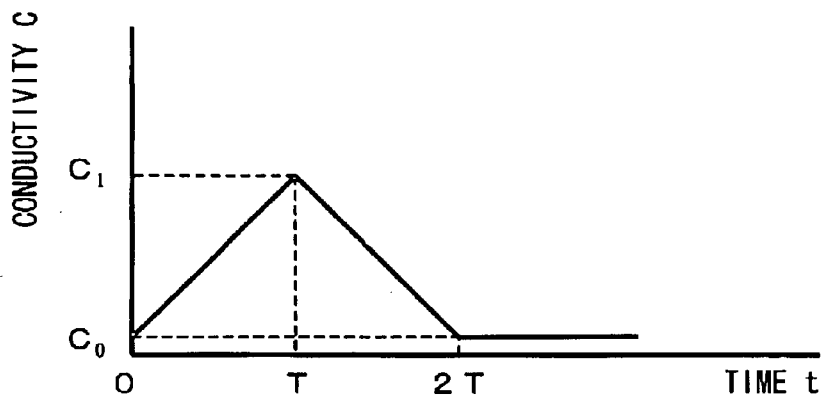
FIG. 4A and FIG. 4B are drawings for explaining the operation of the organic carbon content measuring apparatus according to the embodiment shown in FIG. 1.
Figure 4B:
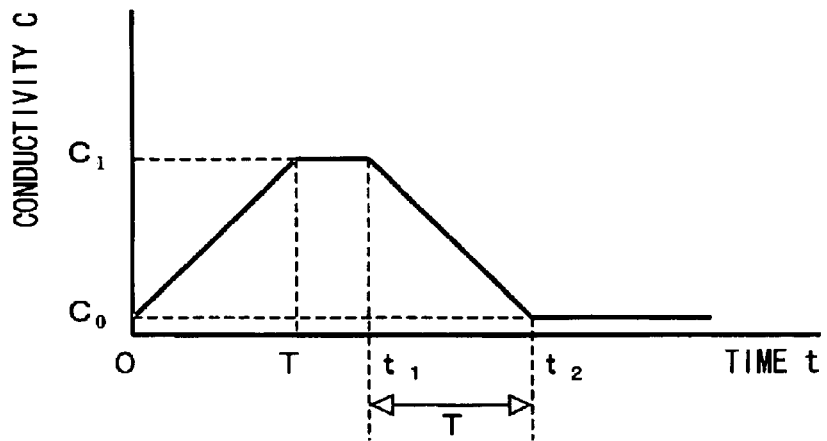
Figure 4C:
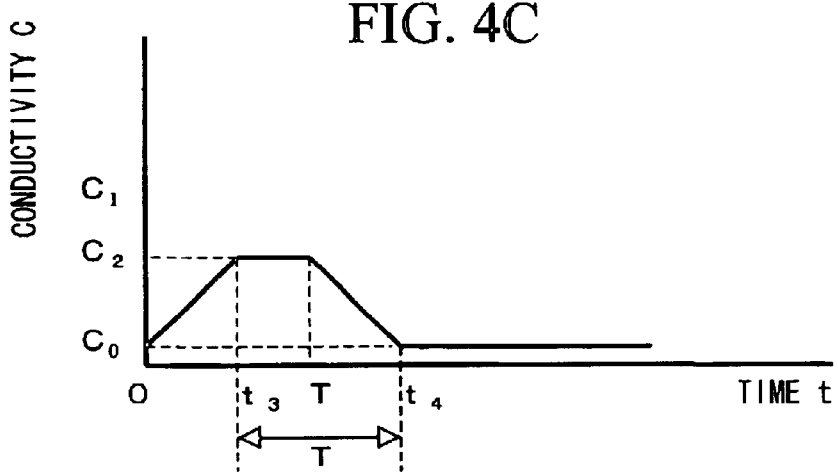
FIG. 4C is a drawing for explaining the inadequate operation of the organic carbon content measuring apparatus according to the embodiment shown in FIG. 1.

In the case that the apparatus shown in FIG. 1 is operated at a constant rate of flow F, the relationship between the conductivity C detected by the conductivity detecting electrode 3 and the time after the light is turned on is shown in FIG. 4A to FIG. 4C, depending on the rate of flow F.

First, FIG. 4A shows the change in conductivity in the case that $F=V/T$. In this case, the portion of test liquid that was at the entrance of the UV light irradiation area at the time the light was turned on arrives at the exact position of the conductivity detecting electrode 3 when the light is turned off (t=T). In addition, the portion of test liquid that was at the entrance of the UV light irradiation area when the light was turned off arrives at the exact position of the conductivity detecting electrode 3 at time t=2T. This means that the portion of test liquid that was irradiated by UV light the longest time (T) arrives at the position of the conductivity detecting electrode 3 at time t=T, and the portion of test liquid that was not similarly UV irradiated at time t=0 arrives at t=2T. Moreover, while t is 0 to T, the portion of test liquid that was UV oxidized during time interval t arrives at the conductivity detecting electrode 3, and when t is T to 2T, the portion of the test liquid that was UV oxidized during time interval (2T−t) arrives at the conductivity detecting electrode 3. In addition, because the conductivity rises along with the progress of the UV oxidizing, as shown in the figure, at t=T, the conductivity C changes to reach the maximum value $C_1$, which depends of the amount of organic carbon.

Next, FIG. 4B shows the change in conductivity in the case that $F<V/T$. In this case, when the light is turned off (t=T), the portion of test liquid that was already flowing into the UV light irradiation area 2 when the light was turned on arrives at the conductivity detecting electrode 3. In addition, the portion of test liquid that was at the entrance of the UV light irradiation area when the light was turned on arrives at the position of the conductivity detecting electrode 3 at t=$t_1$ after the light is turned off (t=T). In addition, the portion of the test liquid that was at the entrance to the UV irradiation area while the light was turned off arrives exactly at the position of the conductivity detecting electrode 3 at t=$t_2$ (=$t_1$+T). That is, the portion of test liquid that was UV oxidized for the longest time (T) continues to arrive at the position of the conductivity detecting electrode 3 while t is T to $t_1$, and the portion of test liquid that was not similarly irradiated at t=0 arrives at t=$t_2$. Moreover, while t is 0 to T, the portion of test liquid that was UV oxidized during time interval t arrives at the conductivity detecting electrode 3, and while t is $t_1$ to $t_2$, the portion of test liquid that was UV oxidized during time interval ($t_2$−t) arrives at the conductivity detecting electrode 3. Thus, the conductivity C, as shown in the figure, maintains the maximum value $C_1$ while t is T to $t_1$.

In contrast, for the sake of comparison, FIG. 4C shows the change in conductivity in the case that $F>V/T$. In this case, the portion of test liquid that was at the entrance of the UV light irradiation area when the light was turned on arrives at the position of the conductivity detecting electrode 3 at time t=$t_3$ before the light is turned off (t=T). The portion of test liquid that was still upstream from the UV light irradiation area 2 when the light was turned on arrives at the position of the conductivity detecting electrode 3 when the light is turned off (t=T). In addition, the portion of test liquid that was at the entrance of the UV light irradiation area when the light was turned off arrives at the exact position of the conductivity detecting electrode 3 at t=$t_4$ (=$t_3$+T). This means that while t is $t_3$ to T, the portion of test liquid that was UV oxidized for a time shorter than T continues to arrive at the conductivity detecting electrode 3. Moreover, while t is 0 to $t_3$, the portion of test liquid that was UV oxidized during time interval t arrives at the conductivity detecting electrode 3, and while t is T to $t_4$, the portion of test liquid that was UV oxidized during time interval ($t_4$−t) arrives at the conductivity detecting electrode 3. Thus, as shown in the figure, the conductivity C maintains the maximum value $C_2$ while t is $t_3$ to T, but $C_2$ becomes a value smaller than $C_1$. Moreover, $C_2$ becomes smaller as F becomes larger.

This means that in the range of the condition of the rate of flow F ($F \leq V/T$) shown in FIGS. 4A and 4B, the maximum value $C_1$ of the conductivity is obtained, and even if the rate of flow F fluctuates, only the time it takes to reach the value of $C_1$ fluctuates. Thus, even if the rate of flow fluctuates, the difference between the maximum conductivity $C_1$ and the base conductivity $C_0$ is obtained based on identical oxidization conditions, and the amount of the organic carbon in the test liquid can be found from this value.

Figure 5A:
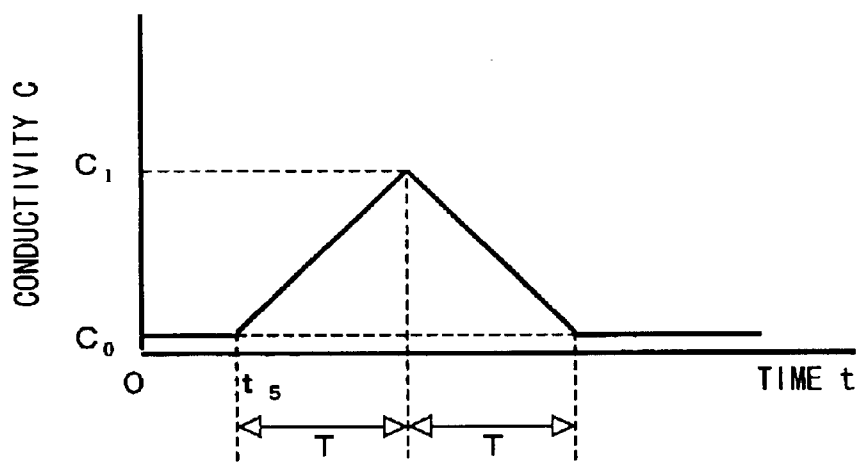
FIG. 5A and FIG. 5B are drawings for explaining the operation of the organic carbon content measuring apparatus according to the embodiment shown in FIG. 2 and FIG. 3.
Figure 5B:
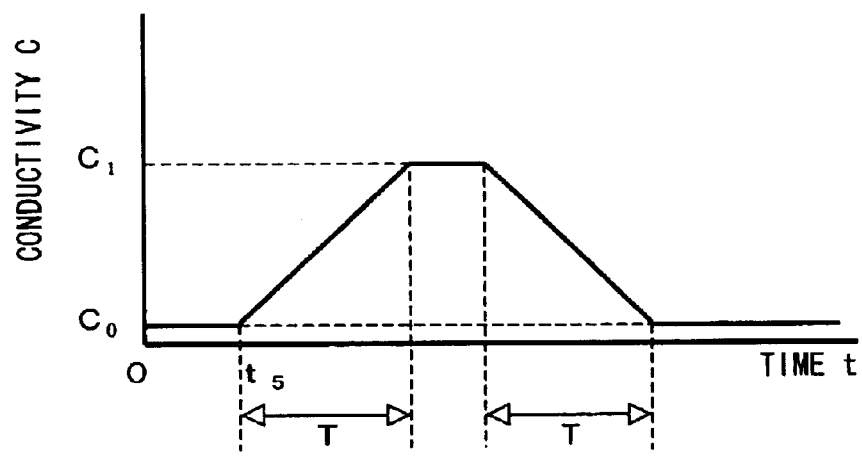
Figure 5C:
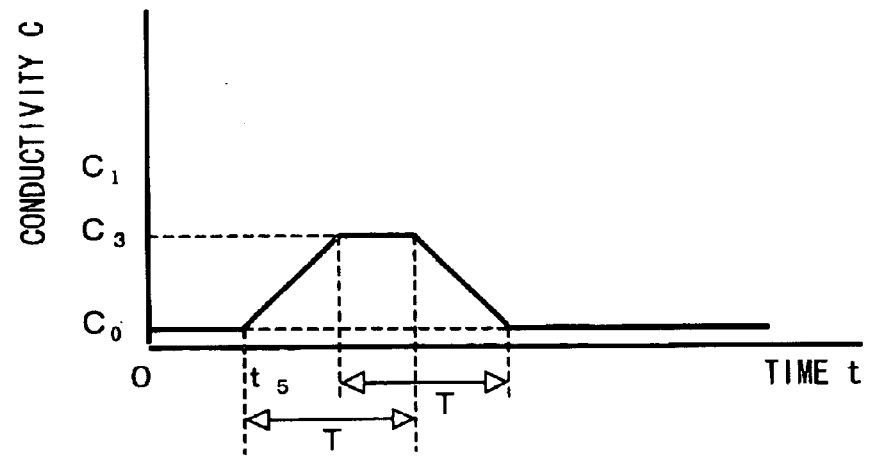
FIG. 5C is a drawing for explaining inadequate operation of the organic carbon content measuring apparatus according to the embodiments shown in FIG. 2 and FIG. 3.

Next, the relationship between the conductivity C detected by the conductivity detecting electrode 3 and the time interval t after the light is turned on is shown in FIG. 5A to FIG. 5C in the case of operating the apparatus shown in FIG. 2 and FIG. 3 at a constant rate of flow F. Similar to FIG. 4A to FIG. 4C, in FIG. 5A to FIG. 5C, FIG. 5A shows the change in conductivity in the case that $F=V/T$, FIG. 5B shows the change in conductivity in the case that $F \leq$(less than) V/T, and FIG. 5C shows the change in conductivity in the case that $F \geq$(greater than) V/T.

In all the cases FIG. 5A to FIG. 5C, a response is obtained that lags behind the corresponding FIGS. 4A to 4C by the time interval $t_5$, which is the time interval during which the test liquid moves from the exit of the UV irradiation area 2 to the conductivity detecting electrode. Moreover, in the case of the apparatus of FIG. 2, $t_5$=Va/F, and in the case of the apparatus of FIG. 3, $t_5$=Vb/F. This means that in order to obtain data of the maximum conductivity $C_1$ by making $t_5$ smaller and faster, preferably an apparatus in which Va and Vb are made as small as possible should be made.

For the sake of explanation, FIGS. 4A to 4C and FIGS. 5A to 5C are disclosed as having a constant rate of flow F, but preferably after obtaining the maximum conductivity $C_1$, F is set to a high rate of flow, and the replacement of the test liquid and the expelling of bubbles is carried out. Thereby, the conductivity C is quickly restored to the base conductivity $C_0$, and the next measurement can be commenced quickly.

Switching to the high rate of flow can be carried out by anticipating the time needed to determine that the maximum conductivity $C_1$ has been reliably obtained, or at a specified time interval. In addition, to carry out the restoration to the base conductivity $C_0$ more quickly, detection of the obtaining of the maximum conductivity $C_1$ is performed, and at that time switching can be immediately performed. To detect that the conductivity has become the maximum, methods that recognize that the rate of change (differential value) of the conductivity C has fallen below a predetermined value, for example, as is typically carried out, can be considered. In addition, using the fact that the temperature of the test liquid fluctuates slightly due to the heat generation of the UV light source, it may be determined that the maximum conductivity $C_1$ has been obtained when the temperature has reached the maximum value.

As described above, in the case that the conductivity reaching the maximum is detected using the conductivity or temperature, from the time until this is detected, the approximate value of the rate of flow F is known, and if, in the case that $F \leq V/T$ does not hold (in the case of the embodiment in FIG. 1, the case that the conductivity reaches its maximum during a time interval shorter than T, as shown in FIG. 4C), a warning can be output, for example, as a response. Moreover, as a means for confirming the rate of flow F, of course a flow meter can be provided separately.

Moreover, when comparing the embodiments of FIG. 1 to FIG. 3, the configuration in which the conductivity detecting electrode 3 is disposed outside the oxidizing process vessel 1 is not limited, as shown in FIG. 3, to the specific structure of the conductivity detecting electrode 3 or the concrete structure of the oxidizing process vessel 1, and thus generally can be easily manufactured. However, as methods for simply reducing the time until the maximum conductivity is obtained, using FIG. 2 is preferable to using FIG. 3, and using FIG. 1 is preferable to using FIG. 2. In addition, in the case of using the configuration of FIG. 1, the UV light also irradiates the conductivity detecting electrode 3 as well, and thus has the advantage that contaminants that can hinder the conductivity detection adhere with difficulty.

EXAMPLES

Figure 6:
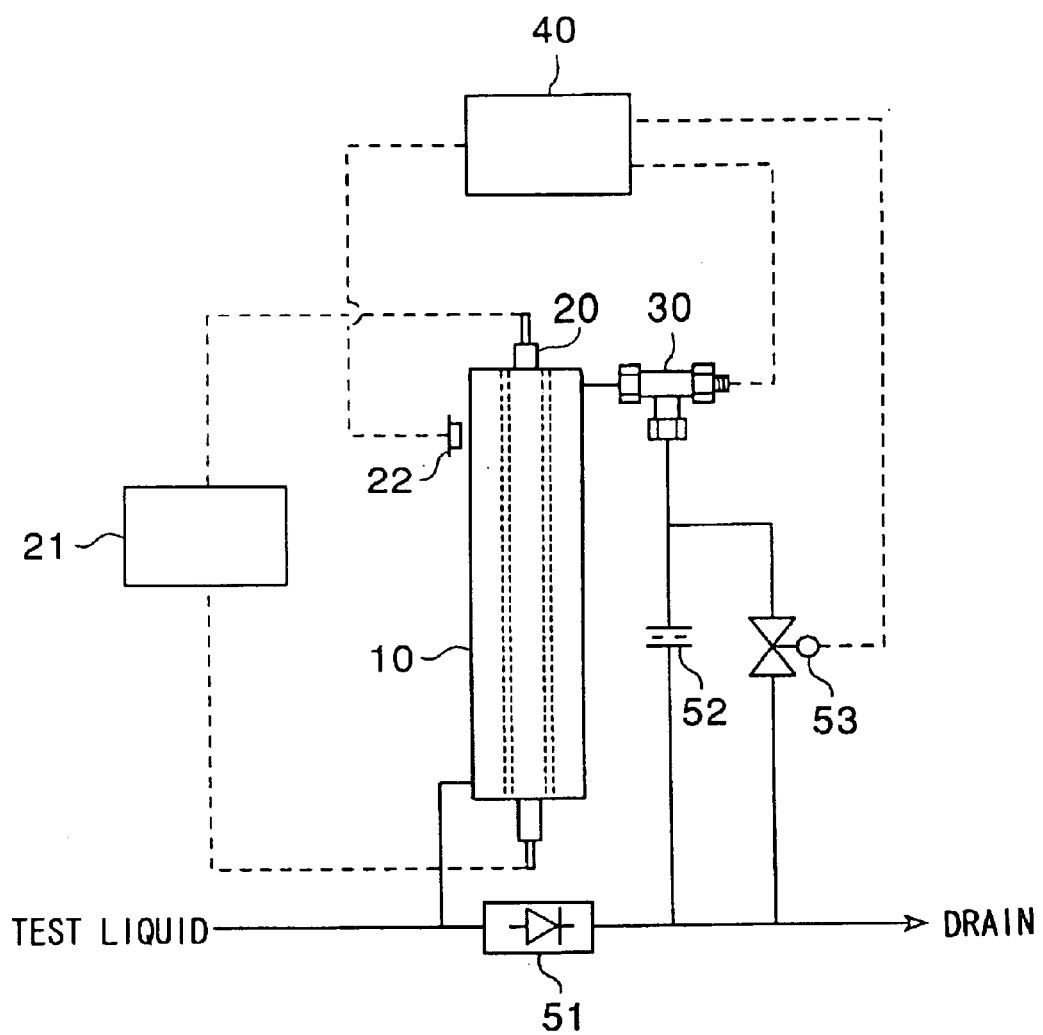
FIG. 6 is a structural drawing showing an organic carbon content measuring apparatus according to an example of the present invention.

FIG. 6 shows an example of the present invention. The organic carbon content measuring apparatus shown in FIG. 6 comprises an oxidizing process vessel 10, a UV light source 20 that irradiates the test liquid in the oxidizing process vessel 10 with UV light from within, a lighting control means 21 that extinguishes this UV light source 20 after lighting it for a fixed time interval, a photodiode 22 that serves as a photometer that measures the amount of light of the UV light source 20, a conductivity detecting electrode 30 having a built-in temperature sensor provided downstream from the exit of the oxidizing process vessel 10, and a calculating apparatus 40 that inputs the data of this conductivity detecting electrode 30 and the data of the photodiode 22.

In addition, the present apparatus provides a flow rate control means comprising a pressure regulating valve 51, an orifice 52, and a normally closed valve 53. The pressure regulating valve 51 allows the test liquid equal to or greater than a fixed pressure escape to a drain, and at the entrance pipe of the oxidizing process vessel 10 that separates upstream, regulates the test liquid such that it will be supplied at a pressure in a fixed range. The orifice 52 is provided at the drainage flow path downstream from the conductivity detecting electrode 30. Thereby, using back-pressure regulation by the orifice 52 and supply pressure regulation by the pressure regulating valve 51, the rate of flow F of the test liquid, the volume of the UV irradiation area in the oxidizing process vessel 10, and the irradiation time T of the UV light are adjusted so as to maintain the relationship $F \leq V/T$. In addition, the normally closed valve 53 is installed on the flow path parallel to the flow path on which the orifice 52 is installed, and opens and closes in response to a command from the calculating apparatus 40. In addition, in the case that the normally closed valve 53 is open, a rate of flow F significantly larger than V/T can be obtained.

Figure 7A:
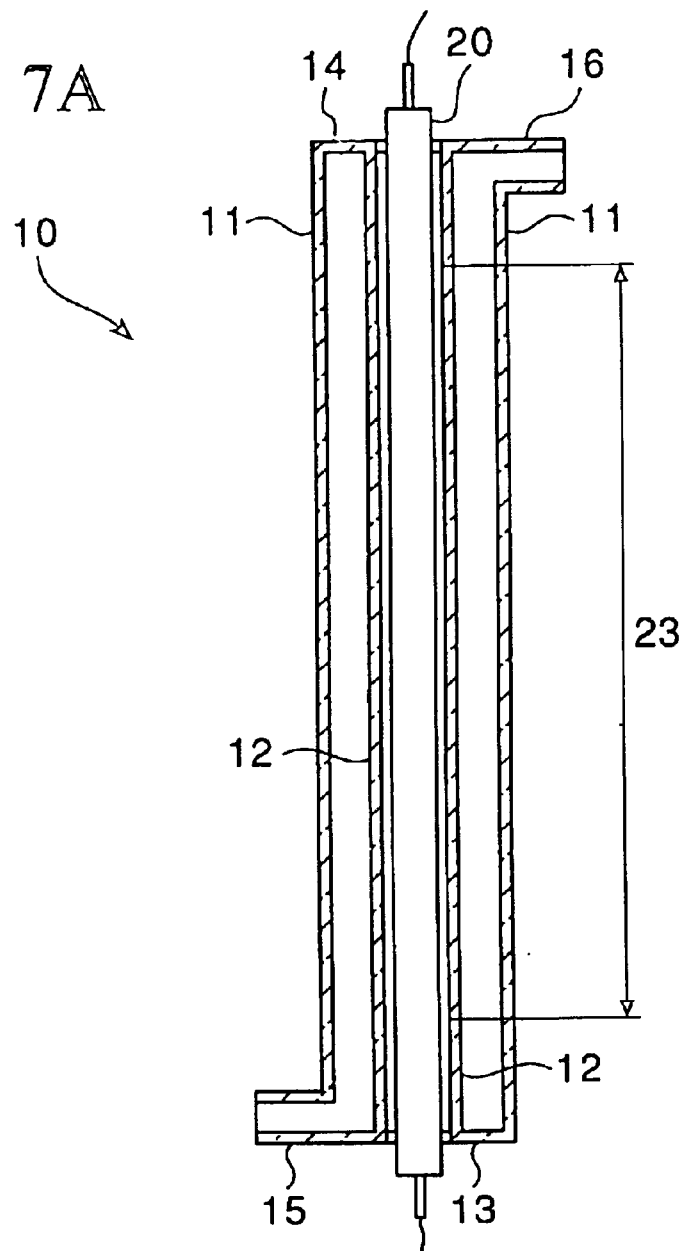
FIGS. 7A and 7B are concrete examples of the oxidizing process vessel used in the organic carbon content measuring apparatus according to an example of the present invention.
Figure 7B:
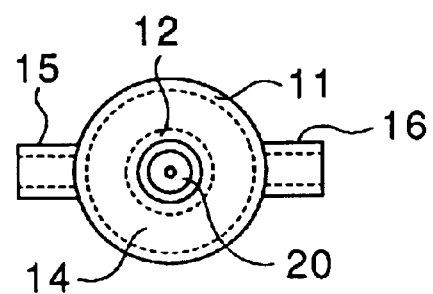

A concrete example of the structure of the oxidizing process vessel 10 will be explained based on FIGS. 7A and 7B. The oxidizing process vessel 10 in FIGS. 7A and 7B has an external tube 11 and an internal tube 12, with a ring shaped lower base wall 13 and an upper base wall 14 that each connect to one of the ends thereof, thereby forming a space having a double tube structure. In addition, an entrance pipe 15 and an exit pipe 16 are provided in order to allow the test liquid flow into and flow out of this space. The inner wall surface of this external tube 11 is coated with titanium oxide. In addition, the inner tube 12 is formed by a material that allows passage of UV light, such as quartz glass, and is not coated with titanium oxide, etc. In FIGS. 7A and 7B, the UV light source 20 is inserted into the inner tube 12 of the oxidizing process vessel 10, and the test liquid that passes through the irradiation area 23 impinged on by the UV light from this UV light source 20 is oxidized by the UV light.

Figure 8A:
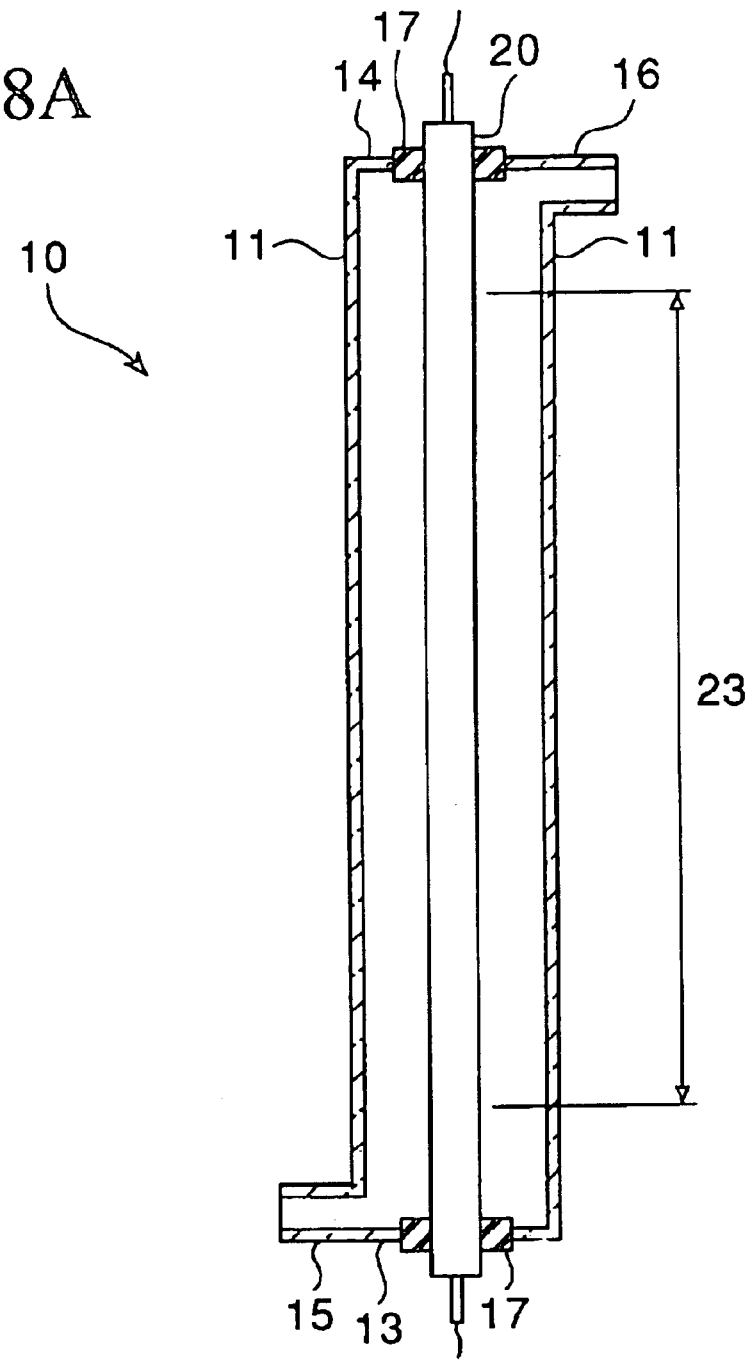
FIGS. 8A and 8B are concrete examples of the oxidizing process vessel used in the organic carbon content measuring apparatus according to an example of the present invention.
Figure 8B:
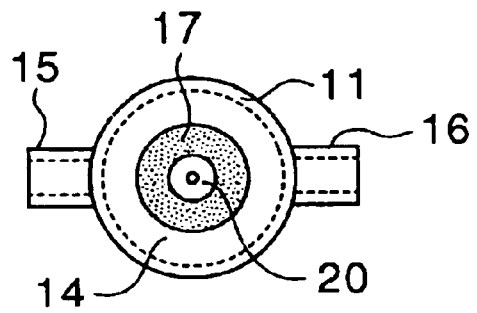

Another concrete example of the oxidizing process vessel 10 is explained based on FIGS. 8A and 8B. The oxidizing process vessel 10 of FIGS. 8A and 8B has an external tube 11 and ring shaped lower base wall 13 and upper base wall 14 on the ends thereof. In addition, the UV light source 20 is inserted watertight inside the outer tube 11 using packing between the lower base wall 13 and the upper base wall 14 of the oxidizing process vessel 10, and the outer tube of the UV light; source 20 also serves as the inner tube of the oxidizing process vessel 10. Thus, the outer tube 11, the outer tube of the UV light source 20, the lower base wall 13, and the upper base wall 14 together form the space of a double-layered tube structure, and the test liquid in this space flows in from the entrance tube 15 and flows out from the exit tube 16. The inner surface of the outer tube 11 is coated with titanium oxide. In this case as well, the test liquid passing through the irradiation area 23 impinged on by the UV light from the UV light source 20 is oxidized.

In FIGS. 7A and 7B, and FIGS. 8A and 8B, the UV light arrives at the outer tube coated with titanium oxide without any substantial interruptions, and the oxidization reaction of the test liquid that is in contact hereto can be efficiently promoted. In addition, when the outer tube is coated with titanium oxide, it has been confirmed that the UV light leaks with difficulty from the outer tube to the outside. This means that the energy of the UV light is expended almost entirely for the oxidization reaction without leaking to the outside. In addition, there is no leakage of the UV light to the outside, damage to the peripheral devices, or deleterious influence to the operators. Furthermore, the UV light source 20 is inserted into the oxidizing process vessel 10, and a layer of liquid comprising the test liquid encloses the outside thereof, and thus the temperature fluctuation of the UV light source is suppressed to a small level, and the stability of the UV light source can be increased.

Figure 9:
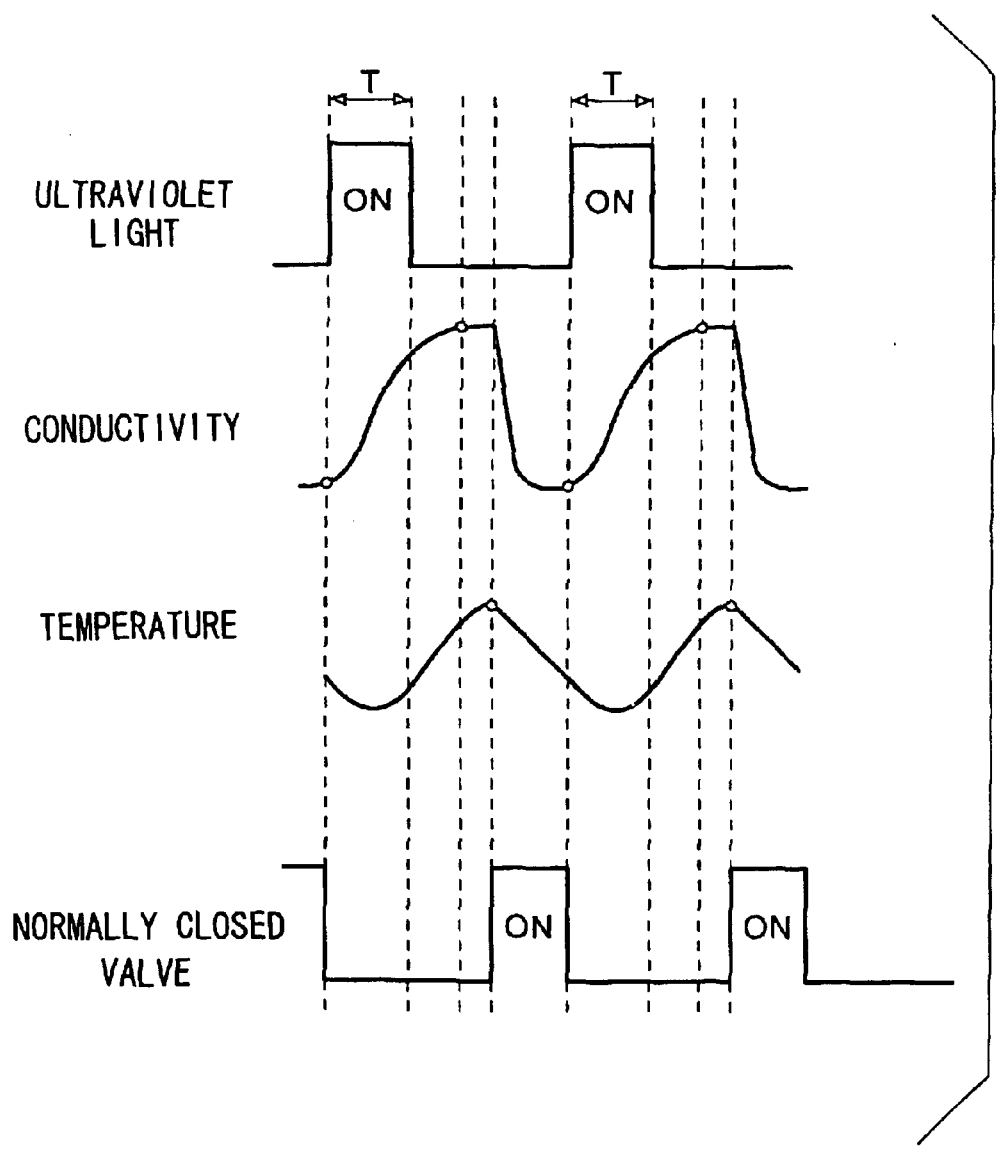
FIG. 9 is a drawing for explaining the operation of the organic carbon content measuring apparatus according to an example of the present invention.

The operation of the organic carbon content measuring apparatus shown in FIG. 6 will be explained using FIG. 9. First, the normally closed valve 53 is turned off and closed, and the test liquid flows into the oxidizing process vessel 10 at a flow rate $F \leq V/T$. At the same time that the normally closed valve 53 is turned off, the lighting of the UV light source 20 starts, to be extinguished after the passage of a time interval T. During this interval, the conductivity detected by the conductivity determining electrode 30 gradually rises depending of the state of the oxidization of the portion of test liquid passing through, and finally, the maximum conductivity, which depends on the lighting time of the UV light source 20 and the organic carbon content, becomes constant. During this interval, the temperature of the test liquid rises during lighting and falls while the light is extinguished due to the influence of the heat generated by the UV light source. The temperature detected by the temperature sensor in the conductivity detecting electrode 30 lags behind the lighting and extinguishing of the UV light source due to the time that the portion of the test liquid exiting the UV light irradiation area takes to reach the conductivity detecting electrode 30 and a slight response time, and thus can be observed to rise and fall as shown in the figures.

Next, when the normally closed valve 53 is turned on and opened, a large portion of the test liquid flowing out from the oxidization process vessel 10 passes through the normally closed valve 53, and thus the rate of flow of the test liquid flowing into oxidizing process vessel 10 rapidly increases. The timing for turning on this normally closed valve 53 can be uniformly controlled, taking into account the available time, or be preformed at the point in time when the rise in conductivity is confirmed to be below a fixed value. In addition, the maximum value of the temperature can be obtained after the maximum value of the conductivity is obtained, and thus the normally closed valve 53 can be turned on at the point in time that the temperature reaches a maximum. As shown in the figure, when the normally closed valve 53 is turned on, the conductivity rapidly falls and the base conductivity is restored.

In addition, after the conductivity is restored to the base conductivity, the normally closed valve 53 is again turned off, and the above operation is repeated. The timing for turning the normally closed valve 53 off again can also be uniformly controlled, taking into account the available time, or can be performed at the point in time when the fall in conductivity is confirmed to be below a fixed value.

The data for the base conductivity and maximum conductivity obtained in this manner is input into the calculation apparatus 40. Then, the organic carbon content is calculated after temperature compensation based on the data of the temperature sensor. In addition, when the value of the photometer 22 becomes smaller than a predetermined value, the UV light source 20 is determined to be deteriorating, and a warning can be issued from the calculating apparatus 40.

Figure 10:
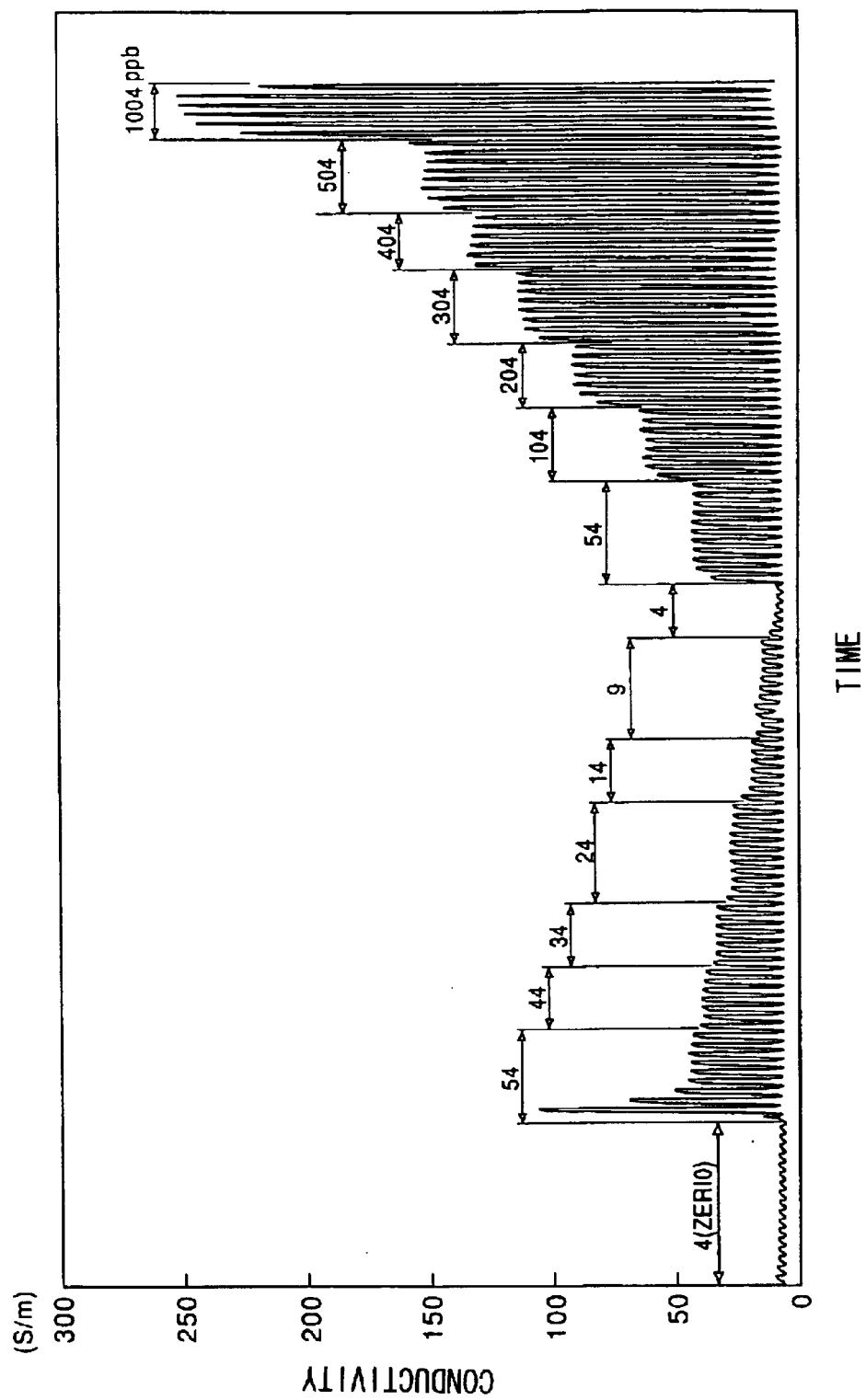
FIG. 10 is data showing methanol reference liquid measured with the organic carbon content measuring apparatus according to an example of the present invention.

FIG. 10 shows the experimental values obtained using an apparatus equivalent to that in FIG. 6. However, because the supply pressure of the reference liquid used as the test liquid was insufficient, in place of the orifice 52, a low flow rate pump was used. In addition, in place of a normally closed valve 53, a high flow rate pump was used, and when this pump was turned on, the rate of flow of the test liquid in the oxidizing apparatus 10 is increased, and the test liquid can be replaced.

The specific conditions in which these experimental values were obtained are as follows. First, the structure of the oxidizing process vessel 10 is the one shown in FIG. 7A and FIG. 7B. The inner diameter of the outer tube is 18 mm, the outer diameter of the inner tube is 16 mm, the total length is 225 mm, and the total volume is 12 mL. The irradiation area 23 therein is positioned substantially at the center in the lengthwise direction, having a length of 160 mm and a volume V of 8.5 mL. A conductivity detecting electrode 30 used is a flow cell type having an volume of approximately 1 mL and having a cell constant of approximately 0.1. An approximately 25 mm Teflon tube with an inner diameter of 4 mm communicates between the oxidizing process vessel 10 and the conductivity detecting electrode 30. As a UV light source 20, a low pressure mercury lamp having a 5W rating was used, and it was repeatedly lit for 90 seconds (T=1.5 min), and then extinguished for 115 seconds.

The test liquid was regulated so as to pass through the oxidization process vessel 10 at a rate of flow F of approximately 4–5 mL/min when the high flow rate pump is turned off, so as to satisfy $F \leq V/T = 8.5$ mL/1.5 min=5.7 mL/min. In addition, the test liquid was regulated so as to pass through the oxidization process vessel 10 at a rate of flow of approximately 70 mL/min when the high flow rate pump is turned on. The high flow rate pump is turned off at the same time that the UV light source is turned on, and 150 seconds later is turned on for 55 seconds. This operation is performed repeatedly.

As a test liquid, a 4 to 1004 ppb (as carbon, and similarly hereinafter) reference liquid was supplied that was prepared by the method of merging while regulating the flow rate ratios of a flow of a 1000 ppm methanol reference liquid and a flow of water for dilution that includes 4 ppm of organic carbon. The numbers shown in FIG. 10 are test liquid concentrations (unit: ppb) when each peak data was obtained.

Figure 11:
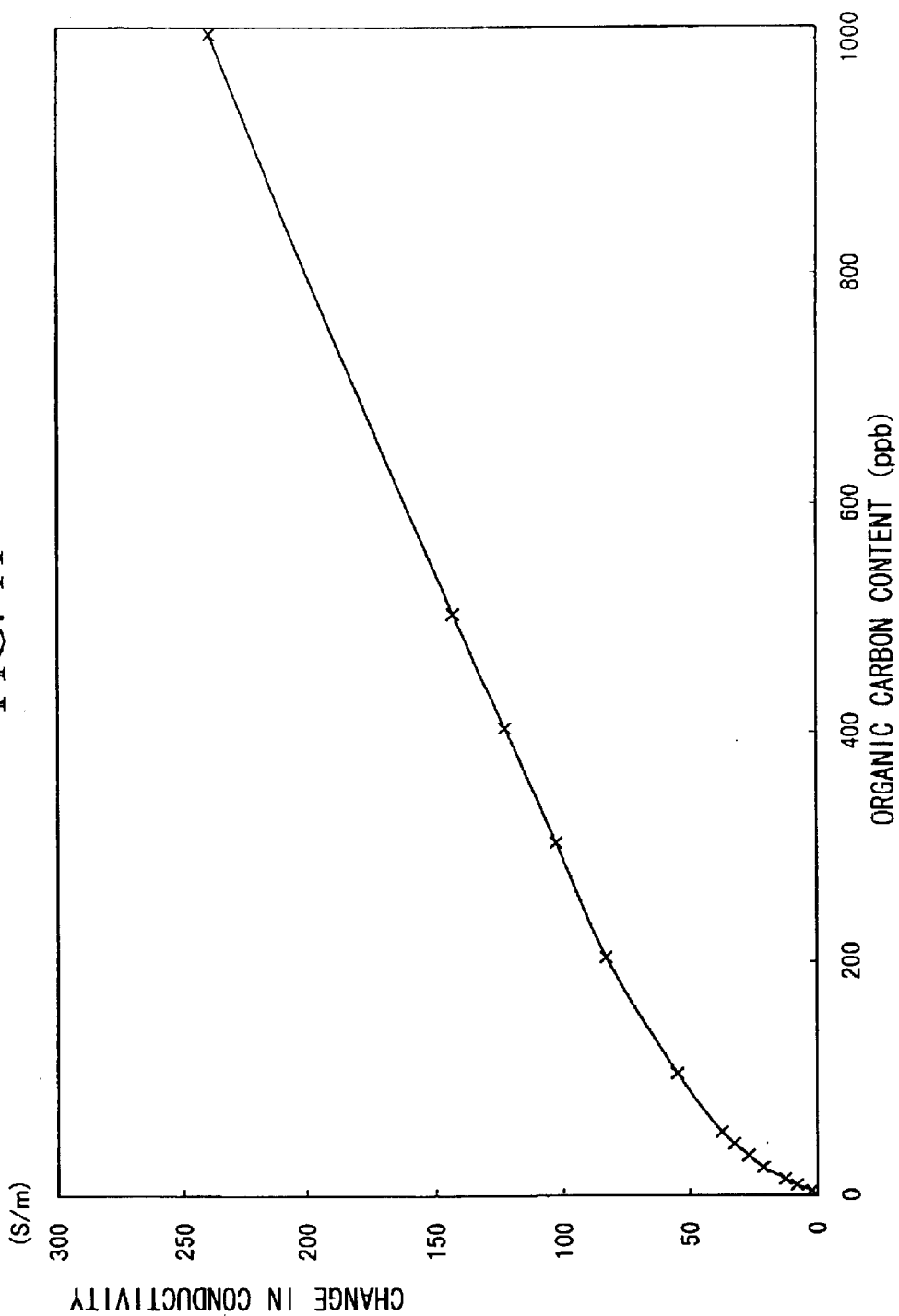
FIG. 11 is a calibration curve found from the data in FIG. 10.

As shown in FIG. 10, good repeatability of the peak of the conductivity according to each concentration is obtained at intervals of 205 seconds (about 3.5 minutes). In addition, from the data in FIG. 10, the relationship of the change in conductivity (the difference between the maximum conductivity and the base conductivity) relative to the concentration of the test liquid can be found, and, as shown in FIG. 11, a favorable calibration curve is obtained. Moreover, in FIG. 10, a minor deterioration of the peak value can be seen when switching the concentration of the test liquid, but this is considered to be a problem of the replacement lag on the part of the test liquid preparation rather than a problem on the part of the apparatus.

Figure 12:
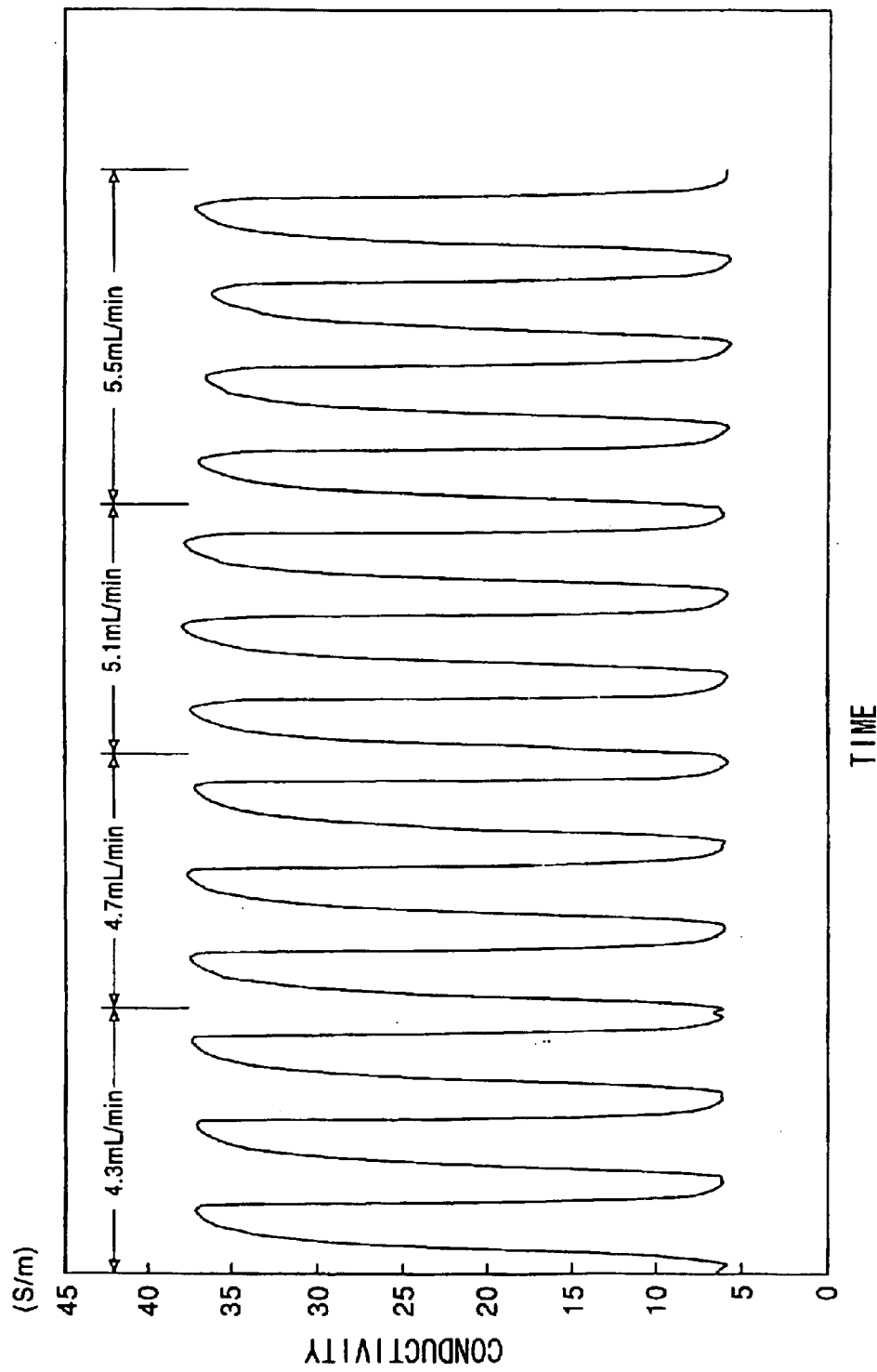
FIG. 12 is data showing the influence of fluctuation in the rate of flow in the organic carbon content measuring apparatus according to an example of the present invention.

Next, in order to find the influence of the flow rate of the test liquid, the rate of flow F of the low flow rate pump (the rate of flow when the high flow rate pump is turned oft) was varied between 4.3 mL/min to 5.5 mL/min, and a 54 ppb methanol reference liquid prepared in the same manner as described above was measured. The results are shown in FIG. 12. The numbers in FIG. 12 are the values of the rate of flow F when each peak data was obtained. As shown in the figure, in the range satisfying the conditions wherein $F \leq V/T = 8.5$ mL/1.5 min=5.7 mL/min, even though there was fluctuation in the rate of flow, it is confirmed that a constant change in conductivity was obtained.

What is claimed is:

1. A measuring method for the organic carbon content characterized in causing a test liquid to flow into the oxidizing process vessel and stopping the irradiation after the UV light has irradiated this test liquid for a predetermined time which time is insufficient to completely oxidize the organic carbon, measuring the base conductivity prior to commencement of the lighting of said UV light and the maximum conductivity after irradiation has stopped in a conductivity detecting means provided in proximity to an outlet of said oxidizing vessel, and finding the organic carbon content of the test liquid from the difference between this base conductivity and maximum conductivity, wherein the rate of flow F of the test liquid that flows through said oxidizing vessel, the volume V of the part of the oxidizing vessel irradiated by the UV light upstream from said conductivity detecting means, and the irradiation time of T of the UV light have the relationship $F \leq V/T$.

2. A measuring method for organic carbon content according to claim 1 characterized in the test liquid in said oxidizing vessel being exchanged by increasing the rate of flow at which the test liquid passes through the oxidizing vessel after this maximum conductivity is measured by said conductivity detecting means.

3. A measuring method for organic carbon content according to claim 1 characterized in using a photo catalyst to promote the UV oxidization of the organic carbon in said test liquid.

4. A measuring method for organic carbon content according to claim 1 characterized in outputting a warning when that the amount of UV light is measured and the amount of the measured light is less than a predetermined value.

5. A measuring apparatus for organic carbon content comprising an oxidizing process vessel through which the test liquid passes, a UV light source that irradiates the test liquid in the oxidizing process vessel with UV light, a light control means that turns off the UV light source after being lit for a predetermined time, a conductivity detecting means that is provided in proximity to an outlet of said oxidizing process vessel, and a calculating means that calculates the organic carbon content in the test liquid from the difference a base conductivity before commencement of the lighting of said UV light and a maximum conductivity after turning off the UV light source that is measured by this conductivity detecting means, which comprises a flow rate control means that controls the rate of flow F such that the rate of flow F at which the test liquid passes through said oxidizing process vessel, the volume V of the part of said oxidizing process vessel irradiated by the UV light that is upstream from said conductivity detecting means, and the irradiation time T of the UV light have the relationship $F \leq V/T$; and said oxidizing process vessel having an inner tube comprising a material that substantially transmits UV light and an outer tube, and is a two-layer pipe structure in which the test liquid passes through the oxidizing vessel between the outer tube and the inner tube, the inside of the outer tube is covered with photocatalyst for promoting the UV oxidization of the organic carbon in the test liquid in said oxidizing process vessel, and said UV light source is disposed within said inner tube side.

6. A measuring apparatus for organic carbon content according to claim 5 characterized in having a means that exchanges the test liquid in said oxidizing process vessel by increasing the rate of flow of the test liquid passing through said oxidizing process vessel by a flow rate control means after said maximum conductivity is measured by said conductivity detecting means.

7. A measuring apparatus for organic carbon content according to claim 5 further comprising a photometer that measures the amount of UV light from the UV light source.

8. A measuring apparatus for organic carbon content according to claim 5 further comprising a means for confirming the rate of flow F of the test liquid in said oxidizing process vessel.

9. A measuring apparatus for organic carbon content comprising an oxidizing process vessel through which the test liquid passes, a UV light source that irradiates the test liquid in the oxidizing process vessel with UV light, a light control means that turns off the UV light source after being lit for a predetermined time, a conductivity detecting means that is provided in proximity to an outlet of said oxidizing process vessel, and a calculating means that calculates the organic carbon content in the test liquid from the difference between a base conductivity before commencement of the lighting of said UV light and a maximum conductivity after turning off the UV light source that is measured by this conductivity detecting means, which comprises a flow rate control means that controls the rate of flow F such that the rate of flow F at which the test liquid passes through said oxidizing process vessel, the volume V of the part of said oxidizing process vessel irradiated by the UV light that is upstream from said conductivity detecting means, and the irradiation time T of the UV light have the relationship $F \leq V/T$; and said oxidizing process vessel having an outer tube and an inner tube comprising a material that substantially transmits UV light, and is a two-layer pipe structure in which the test liquid passes through the oxidizing vessel between an outer tube and an inner tube, the inside of the outer tube is covered with photocatalyst for promoting the UV oxidization of the organic carbon in the test liquid in said oxidizing process vessel, and said inner tube is formed from the outer tube of said UV light source.

10. A measuring apparatus for organic carbon content according to claim 9 further comprising a means that exchanges the test liquid in said oxidizing process vessel by increasing the rate of flow of the test liquid passing through said oxidizing process vessel by a flow rate control means after said maximum conductivity is measured by said conductivity detecting means.

11. A measuring apparatus for organic carbon content according to claim 9 further comprising a photometer that measures the amount of UV light from the UV light source.

12. A measuring apparatus for organic carbon content according to claim 9 further comprising a means for confirming the rate of flow of the test liquid in said oxidizing process vessel.

13. A measuring apparatus for organic carbon content comprising an oxidizing process vessel through which the test liquid passes, a UV light source that irradiates the test liquid in the oxidizing process vessel with UV light, a light control means that turns off the UV light source after being lit for a predetermined time, a conductivity detecting means that is provided in proximity to an outlet of said oxidizing process vessel, and a calculating means that calculates the organic carbon content in the test liquid from the difference between a base conductivity before commencement of the lighting of said UV light and a maximum conductivity after turning off the UV light source that is measured by this conductivity detecting means, wherein said oxidizing process vessel having an inner tube comprising a material that substantially transits UV light and an outer tube, and is a two-layer pipe structure in which the test liquid passes through the oxidizing vessel between the outer tube and the inner tube, the inside of the outer tube is covered with photocatalyst for promoting the UV oxidization of the organic carbon in the test liquid said oxidizing process vessel, and said UV light source is disposed within said inner tube side.

14. A measuring apparatus for organic carbon comprising an oxidizing process vessel through which the test liquid passes, a UV light source that irradiates the test liquid in the oxidizing process vessel with UV light, a light control means that turns off the UV light source after being lit for a predetermined time, a conductivity detecting means that is provided in proximity to an outlet of said oxidizing process vessel, and a calculating means that calculates the organic carbon content in the test liquid from the difference between a base conductivity before commencement of the lighting of said UV light and a maximum conductivity after turning off the UV light source that is measured by this conductivity detecting means, wherein said oxidizing process vessel having an outer tube and an inner tube comprising a material that substantially transmits UV light, and is a two-layer pipe structure in which the test liquid passes through the oxidizing vessel between an outer tube and an inner tube, the inside of the outer tube is covered with photocatalyst for promoting the UV oxidization of the organic carbon in the test liquid in said oxidizing process vessel, and said inner tube is formed from the outer tube of said UV light source.

* * * * *